United States Patent
Willing et al.

(10) Patent No.: US 7,183,553 B1
(45) Date of Patent: Feb. 27, 2007

(54) GAS DETECTION METHOD AND GAS DETECTION DEVICE

(75) Inventors: Bert Willing, Blonay (CH); Markus Kohli, Grandson (CH); Andreas Seifert, Denens (CH)

(73) Assignee: IR Microsystems SA, Lausanne (CH)

( * ) Notice: Subject to any disclaimer, the term of this patent is extended or adjusted under 35 U.S.C. 154(b) by 23 days.

(21) Appl. No.: 11/227,477

(22) Filed: Sep. 15, 2005

(30) Foreign Application Priority Data

Aug. 4, 2005 (EP) .................................. 05016948

(51) Int. Cl.
G01J 5/02 (2006.01)
(52) U.S. Cl. ................................. 250/339.13
(58) Field of Classification Search ............. 250/338.1, 250/339.06, 339.12, 339.13; 356/437
See application file for complete search history.

(56) References Cited

U.S. PATENT DOCUMENTS

| | | | | |
|---|---|---|---|---|
| 6,064,488 A | * | 5/2000 | Brand et al. | ................. 356/440 |
| 6,172,759 B1 | * | 1/2001 | Goldstein | .................... 356/437 |
| 6,356,350 B1 | * | 3/2002 | Silver et al. | ................. 356/437 |
| 6,995,846 B2 | * | 2/2006 | Kalayeh et al. | ............. 356/437 |

* cited by examiner

*Primary Examiner*—David Porta
*Assistant Examiner*—Marcus Taningco
(74) *Attorney, Agent, or Firm*—Bachman & LaPointe, P.C.

(57) ABSTRACT

The gas detector device comprises at least a VCSEL source and at least a light sensor for detecting a light beam having passed through a sample chamber containing a given gas to be detected. The detection signal of the sensor directly provided to or is time derivated by an electronic derivator and then provided to respective lock-in amplifiers in order to generate a two different 2f-detection, f being the frequency of a wavelength modulation of the source, and thus to provide two corresponding measuring signals the division of which gives a precise value of the gas concentration. The invention uses at least a first modulation reference signal at twice and a second modulation reference signal at twice of the modulation frequency of the laser source. Providing at least a first 2f modulation reference signal has advantages over the prior art, because by using such a reference modulation signal it is possible measure the absolute intensity and therefore to receive the same result at different temperatures or at mode hopping of the laser. A further advantage is that the measurement accuracy is independent from the gas concentration.

8 Claims, 5 Drawing Sheets

GAS DETECTION METHOD AND GAS DETECTION DEVICE

The present invention concerns in particular low-cost infrared (IR) gas detection as disclosed in WO 2005/026705 A1.

The gas detection method and gas detector device as described in this prior art publication is based on a source formed by a wavelength modulated Vertical Cavity Surface Emitting Laser (VCSEL) or Distributed FeedBack (DFB) laser and uses the fact that the modulation of the wavelength is directly connected to a modulation of the laser source output intensity. The intensity of the light having passed the gas volume and being incident to the detector therefore shows a first modulation related to the laser source intensity and a second modulation related to the gas absorption as the wavelength is scanned across the gas absorption line. Accordingly, the known detection method and device provides an initial light signal by a wavelength modulated laser source.

The source provides an initial light signal, which is wavelength modulated with an AC modulation signal at a given initial frequency (f) at the absorption line around the gas to be determined. A light sensor respectively is arranged at the periphery of a detection region intended for receiving at least a gas the concentration of which is to be determined. The light sensor receives a resulting light signal formed by the initial light signal having passed through the detection region. In the following a detection signal is formed which is substantially proportional to the time derivate of the resulting light signal. Further disclosed are first means for generating a first modulation reference signal at the given frequency (f) and second means for generating a second modulation reference signal at twice this frequency (2f). The detection signal is multiplied by the first modulation reference signal and then integrated over time in order to provide a first measuring signal which is a function of the intensity of said initial light signal and substantially independent of the concentration of said gas. The detection signal is further multiplied by said second modulation reference signal and then integrated over time in order to provide a second measuring signal which is a function of the gas absorption and substantially independent of an intensity modulation of the initial light signal at the given initial frequency. The final measuring signal is then received by dividing the second measuring signal by the first measuring signal, thereby providing a signal relative to the concentration or the presence of a given gas. This gas detector method and device have the advantage that only a single sensor unit is needed for one laser source. All necessary information for determining a precise gas concentration value is given by the processing of the generated detection signal which is proportional to the derivate of the light signal received by the sensor unit after having passed through a sample of the defined gas.

The first and second reference modulation signal both are in phase with the intensity variations of the initial light signal. With this known measurement technique the detector signal is time derivated, and the derivated signal is fed into a two-channel lock-in amplifier. The first channel operates on the modulation frequency f, and the output signal is proportional to the slope of the optical power as function of the laser current. The second channel operates of twice the modulation frequency and its output gives a signal, which is proportional to the gas concentration encountered by the laser beam. The ratio of the measuring signal at the frequency 2f to the measuring signal at the frequency f gives the absolute concentration of the gas independent of the laser output as the measuring signal at the frequency f contains information about the laser intensity under the assumption that variations of the laser intensity stem from optical degradations in the light path, such as dust, condensation, speckles. This assumption only holds for two conditions:

1. The laser does not show mode hopping, i.e. sudden changes of wavelength. If such a mode hopping occurs, the wavelength has to be re-adjusted by a change of the DC laser current, which in turn changes the laser output power. With a VCSEL the slope, which is measured by the signal at the frequency f does not necessarily change accordingly. In the case of a DFB laser, the output power is strictly proportional to the DC current which gives the same signal at the frequency f for different output powers.

2. The temperature of the laser is exactly stabilized. For a change of the laser temperature, the wavelength changes, which in turn leads to a re-adjustment of the DC laser current to stay centered on the wavelength of the gas absorption line. Such a change of the current means an intensity change as described in item 1.

With the method described in the prior art patent application, the signal based on a modulation reference signal at the frequency f shows a slope around the center of the gas absorption line, which is proportional to the gas concentration. At high gas concentrations, the accuracy of the measurement is limited by the accuracy of the DC laser current of which the error influences the modulation reference signal at the frequency f. Variations of the current will cause variation of the laser signal, and this effect increases with concentration. This shows, that for some applications the prior art method and device is quite demanding in terms of temperature control of the laser, and depends very much on the thermal mounting of the latter. DFB lasers and VCSEL's differ very much in their thermal budget so that the tracking of the gas absorption line, which is always necessary in term of DC current, has to include a temperature tracking as well.

In view of this, it is the object of the present invention to provide further possibilities for gas detection, which are less dependent from the temperature and sudden wavelength changes.

This problem is solved by the gas detection method and the detector device as claimed. Further advantageous features are described in the respective subclaims.

According to the invention, a first modulation reference signal at twice of said initial frequency is generated by respective means, whereby said first modulation reference signal has a 45° phase angle to said initial light signal. This first modulation reference signal oscillates at an amplitude level between amplitude levels 1 and 0 and is different from the amplitude level of the second modulation reference signal. Finally the detection signal directly received from the resulting light signal is multiplied with the first modulation reference signal.

Thus, the first modulation reference signal is not measured on the frequency f, but on the frequency 2f with a slight modification of the 2f modulation reference signal in the amplitude levels and a phase shifting of 45° between the first modulation reference signal and the initial frequency, which is necessary to provide the same phase which is obtained by a derivate over time. Further, the detector signal is no longer derivated but directly fed to the lock-in amplifier for generating a first measuring signal, which is a function of the intensity of the initial light signal. The resulting signal is directly proportional to the light intensity of the laser as seen by the detector without gas absorption (i.e. including any degradations of the light beam between laser and detector).

Providing a first 2f modulation reference signal has advantages over the prior art, because by using such a reference modulation signal it is possible to measure the absolute intensity and therefore to receive the same result at different temperatures or at mode hopping of the laser. A further advantage is that the measurement accuracy is independent from the gas concentration.

According to the invention, it is possible to combine this first 2f modulation reference signal and its signal treatment with other treatments is order to obtain stable final measuring signals dependent on the special application of gas detection. In a further embodiment of the invention, the second modulation reference signal is generated at twice of said initial frequency f, whereby the first and second modulation reference signals have the same phase correlation to the initial light signal; therefore both signals have 45° phase angle to the AC modulation signal for the laser source. Further, the second modulation reference signal oscillates between amplitude levels 1 and −1. For generating the second measuring signal the detection signal directly received from the resulting light signal is multiplied via lock-in amplifier with said second modulation reference signal. The final measuring signal is obtained by the above-mentioned ratio. In this embodiment the final measuring signal is obtained by a first and a second measuring signal based on a 2f modulation reference signal, both obtained with a detection signal directly received from the resulting light signal.

In a preferred embodiment of the invention the second modulation reference signal is generated at twice of said initial frequency f, whereby said second modulation reference signal is exactly in phase with the intensity variations of said initial light signal. The detection signal is generated by said detection means is substantially proportional to the time derivate of said resulting light signal and the second measuring signal is generated by multiplying said detection signal with said second modulation reference signal. This signal treatment shows the best result, which is independent from the laser temperature and sudden wavelength changes. In this embodiment also the final measuring signal is obtained by a first and a second measuring signal based on a 2f modulation reference signal, but the second measuring signal, which is a function of the absorption is obtained with a derivated detection signal.

In a further embodiment, which needs more electronic parts, two reference modulation signals at a frequency f and 2f are used for generating two measuring signals, which are a function of intensity of the initial light signal. This is realised by generating, additionally to the first measuring signal based on the first 2f modulation reference signal, a third measuring signal, which is also a function of intensity of said initial light signal. This third measuring signal is generated from a detection signal by multiplying the detection signal with a third modulation reference signal at the initial frequency f and then integrated over time. Further the second measuring signal is generated from said detection signal, by multiplying said detection signal with a second 2f modulation reference signal at twice of said initial frequency f and then integrated over time. The third and second modulation reference signals are exactly defined in phase with the intensity variations of said initial light signal and the detection signal for both measuring signals are substantially proportional to the time derivate of the resulting light signal. The final measuring signal is obtained by correlating the first and third measuring signal and generating the ratio between the third measuring signal and the correlated signal of the first and second measuring signal.

In the following other particular features and advantages of the present invention will be described by way of non limiting embodiments with reference to the annexed drawings, in which.

Figure 7:
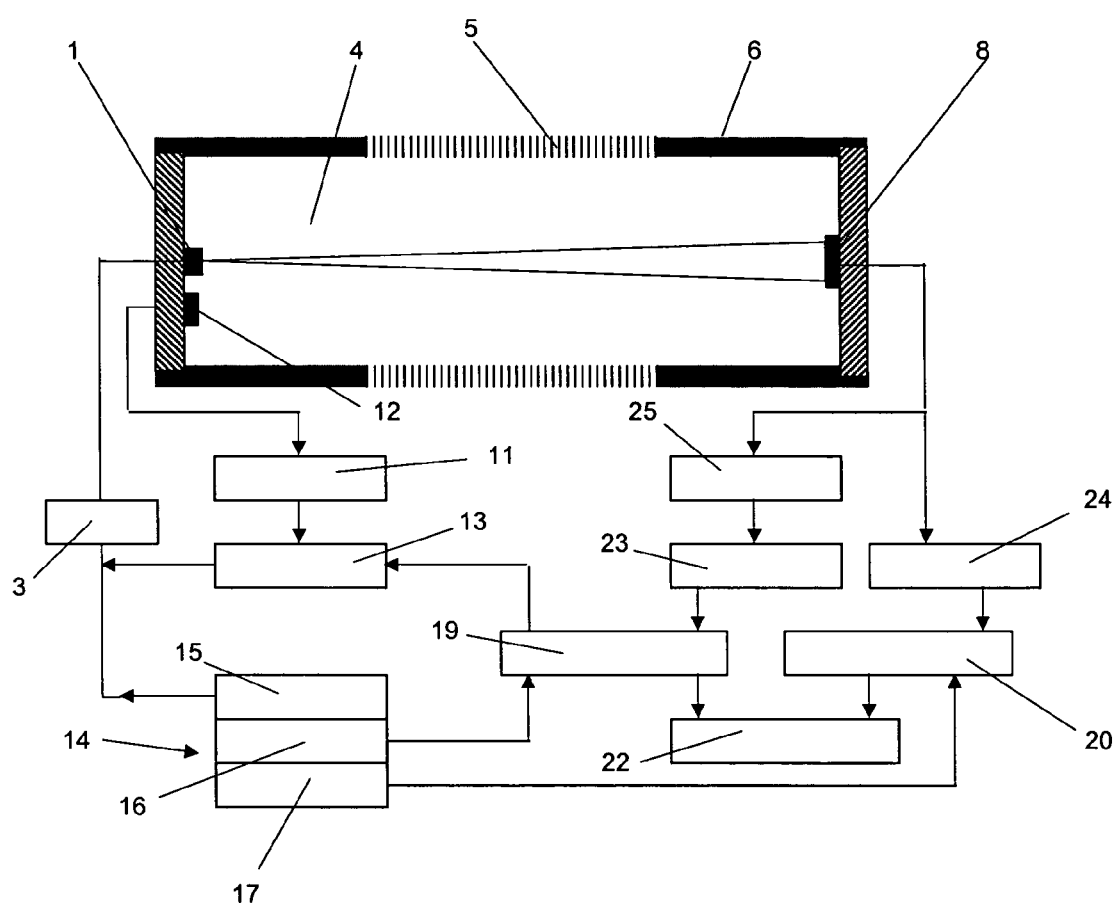
Figure 8:
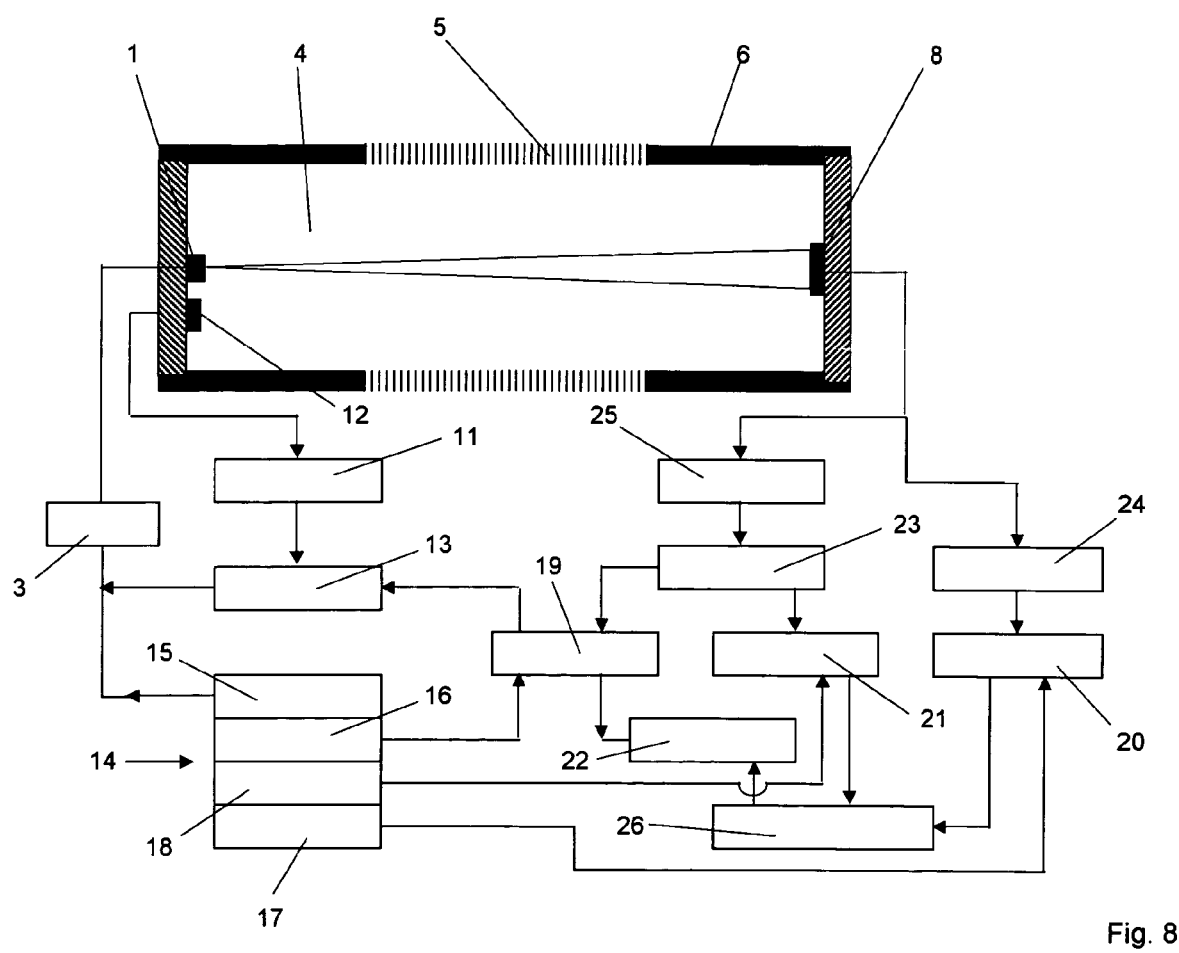

FIG. 7 is a schematic principle view of a second embodiment of the gas detector device according to the present invention using a detection signal directly proportional to the resulting light signal and a detection signal directly proportional to the derivate of the resulting light signal; and FIG. 8 is a schematic principle view of a third embodiment of the gas detector device according to the present invention using a detection signal directly proportional to the resulting light signal and a detection signal directly proportional to the derivate of the resulting light signal, thereby providing a first and second 2f modulation reference signal and a third f modulation reference signal.

In the following, the signal treatment is described in detail as far as it differs from the prior art mentioned in WO 2005/026705 A1. The content of this document is incorporated by reference as far as signal treatment is concerned, which might not be described in this description.

Figure 1:
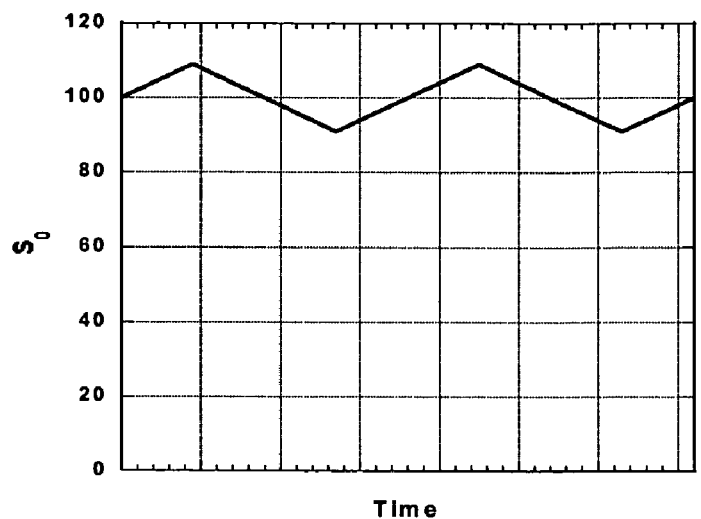
FIG. 1 shows the intensity of the laser light beam entering the sample chamber.
Figure 2:
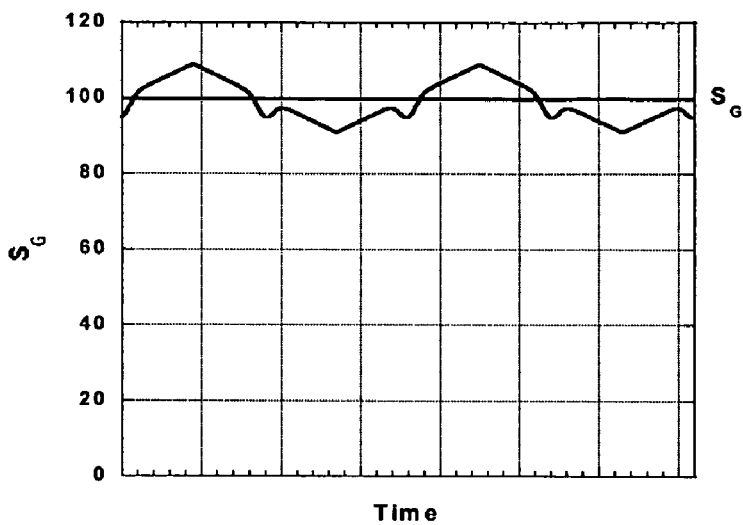
FIG. 2 shows the intensity of the light beam incident on the detector after gas absorption.

As described previously and already mentioned in WO 2005/026705 A1, the laser source is operated with a DC current so that its wavelength corresponds exactly to the center of the gas absorption line. This current is constantly modulated at a frequency f and amplitude such that the wavelength of the laser scans the gas absorption line completely during each cycle by a respective AC modulation signal. FIG. 1 shows the laser output reflected in the initial light signal $S_0$ as a function of time which receives a detection region with the gas to be determined, and FIG. 2 shows the light intensity as a function of time which is incident on the detector in the presence of a given gas concentration, and to which the detector signal $S_G$ is proportional. The waveform of the modulation is chosen here to be triangular; however, the waveform is not of importance to the measurement technique and a sinoidal modulation is actually easier to handle electronically.

Figure 6:
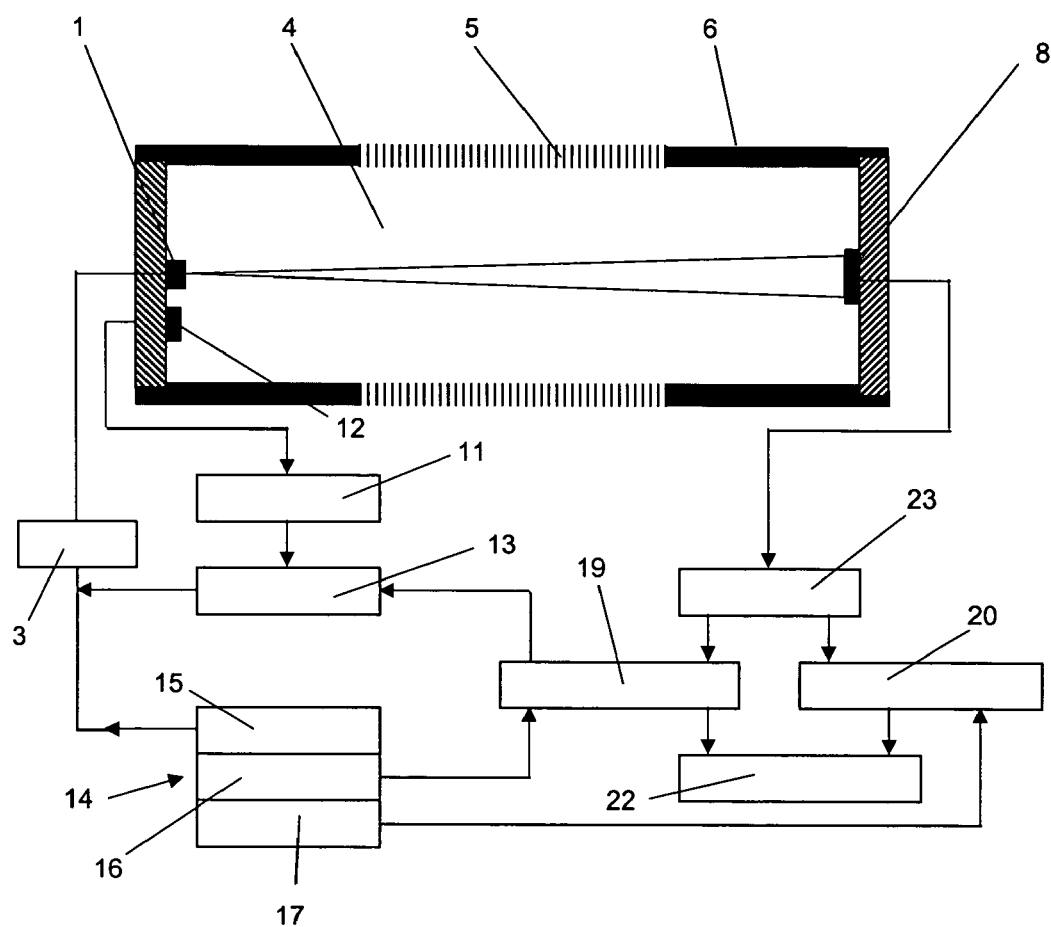
FIG. 6 is a schematic principle view of a first embodiment of the gas detector device according to the present invention using only a detection signal directly proportional to the resulting light signal.

The FIGS. 6 to 8 show three embodiments of a gas detector device of the invention. The common parts of these embodiments are a laser source 1 (it can be also more laser sources and respective sensors) arranged in a laser head of a housing 6. This head further might comprise a sealed cell filled with at least one gas for precisely determined the electrical current value to be furnished the source 1 so that the central wavelength of the provided light peak corresponds to the center of the absorption line of the respective gas, as explained here-before and generally known. Finally the head comprises a temperature sensor 12 electrically connected to temperature means 11. The housing has a sample chamber or gas detection region 4 with gas inlet 5 for the gas to be detected through which the laser beam provided by the laser source 1 pass through. The light sensor 8 receive the laser beam and provides a resulting signal $S_G$ comprising changes in the intensity of the initial light signal $S_0$ due to the gas concentration in the detection region 4 being direct proportional to the intensity. In general, this detection signal $S_G$ as detection signal $S_{D0}$ is directed to at least one lock-in amplifier for generating at least one measuring signal.

The gas detector device of the FIGS. 6 to 8 further comprise electrical supply means 3 for the laser source 1 and DC supply control means 13 for defining a DC current signal for controlling the laser source 1. AC processing means 12 comprise AC supply control means 15 for defining an AC modulation signal at a given reference frequency f generating an alternative scanning around the gas absorption line as explained before. From the AC modulation signal, as known from the prior art, reference modulation signals are generated. The AC processing means further comprise generating means 17 to generate a first reference modulation signal $S_{2f0}$ at twice of said initial frequency, whereby said first modulation reference signal has a 45° phase angle to said initial light signal and oscillates at an amplitude level being different from the amplitude level of the second modulation reference signal between amplitude levels 1 and 0.

Figure 3:
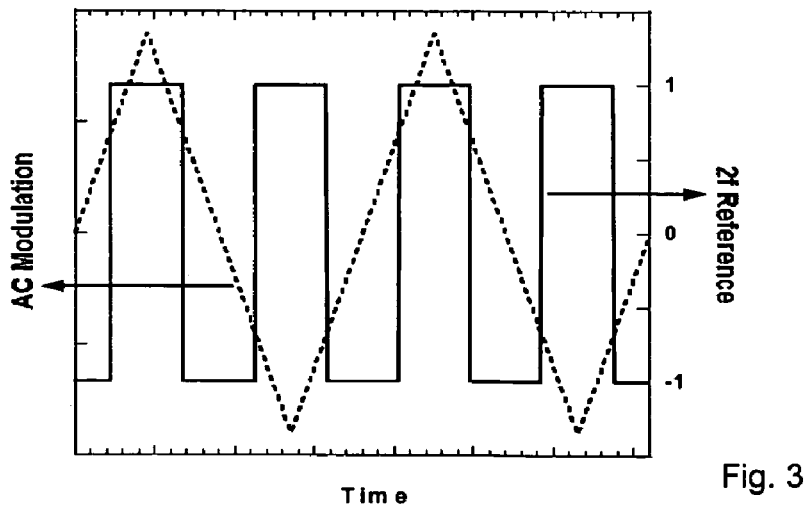
FIG. 3 shows the AC modulation signal and the 2f reference modulation signal as a function of time.

In the embodiment of FIG. 6 two modulation reference signals, a first modulation reference signal $S_{2f0}$ and a second modulation reference signal $S_{2f1}$ on twice the initial modulation frequency f are generated. Latter by the generating means 16. Both reference signals have the same phase correlation to the AC modulation signal as shown in FIG. 3 only for the second modulation reference signal. The difference between the two reference signals is only their amplitude levels: The modulation reference signal $S_{2f1}$ is a rectangular oscillation between the levels 1 and −1, whereas the reference signal $S_{2f0}$ is a rectangular oscillation between the levels 1 and 0.

According to the present invention, these first and second modulation reference signals $S_{2f0}$ and $S_{2f1}$ are respectively provided to two lock-in amplifiers 20 and 19 in which these reference signals are respectively multiplied with the detection signal $S_{D0}$ provided by the light sensor 8 to these two lock-in amplifiers 19, 20 through the preamplifier means 23, and then integrated over several time periods of the AC modulation signal.

Figure 4:
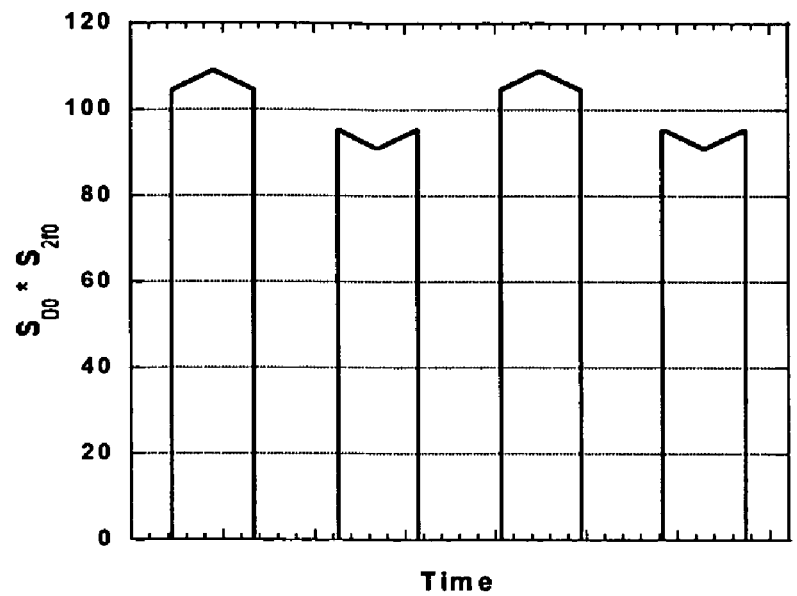
FIG. 4 shows the multiplication of the detection signal directly proportional to the resulting light signal with the first modulation reference signal.
Figure 5:
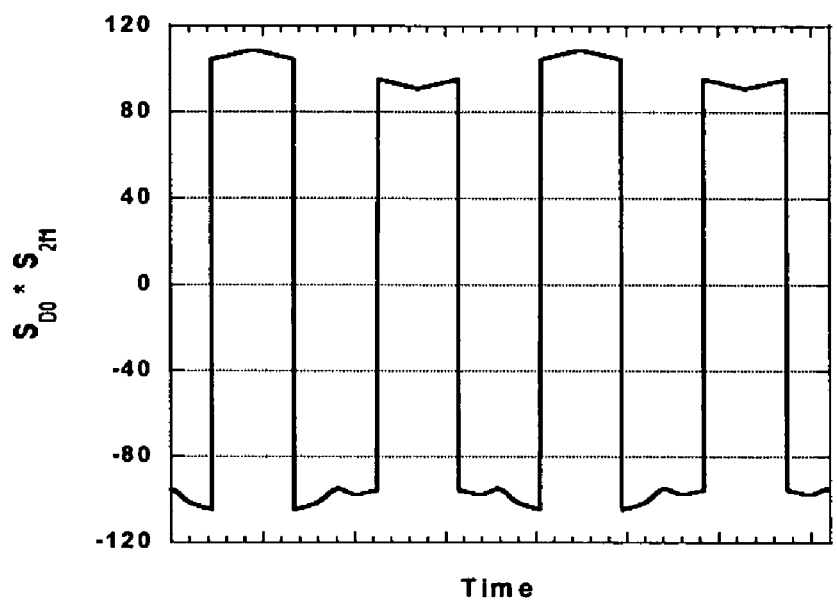
FIG. 5 shows the multiplication of the detection signal directly proportional to the resulting light signal with the second modulation reference signal.

The first lock-in amplifier 20 provides a first measuring signal $S_{MI}$, which is independent from the gas absorption. As seen in FIG. 4, the multiplication with the first modulation reference signal $S_{2f0}$ has the simple effect of cutting out the parts of the detector signal $S_{D0}$ (=$S_G$) containing information on the gas absorption. In this way, the integration over time does not cancel the information on the DC laser intensity, and the output signal is actually the time average of $S_0$ as seen by the light sensor and equals $S_G$ at the center of the gas absorption peak divided by 2. This channel does not correspond to a lock-in detection but rather to a time averaging of a part of the detector signal. At the second lock-in amplifier 19, this corresponds to a 2f-lock-in detection at a phase angle of 45° where the DC part of the light intensity as well as the oscillation on the modulation frequency are cancelled. The result is a measuring signal $S_{MA}$ (FIG. 5), which is proportional to the gas concentration, and implicitly proportional to the laser intensity $S_G$ at the center of the gas absorption peak as seen by the light sensor 8. In the prior art patent application, the same result is obtained with a time derivated detector signal and therefore at a different phase angle.

The final measuring signal is then given as $S_{MA}/S_{MI}$ and is independent of the laser light intensity.

In a preliminary step, the second measuring signal $S_{2f1}$ can be used to define the DC current signal by detecting the maximum of this second measuring signal $S_{2f1}$, when the DC current level is linearly varied. It is to be noted that this preliminary step can be avoided if the device is equipped with a very precise temperature control for the laser source.

The main advantages of this method are that changes of the laser output through temperature variations are compensated and mode hopping of the laser is compensated as long as the gas absorption peak can be tracked. With respect to the prior art, the accuracy of the measurement is independent of the gas concentration. Therefore it is not further necessary to provide a temperature tracking as well, which leads to less cost for a gas detector device.

In the embodiment depicted in FIG. 7, the generating means 16 generate a second modulation reference signal $S_{2f}$, which is exactly in phase with the intensity variations of said initial light signal $S_0$ and a derivator 25 generates a detection signal $S_{D1}$, which is substantially proportional to the time derivate of said resulting light signal generated by the light sensor 8. The derivator 25 is connected with the preamplifier means 23, whereas additional preamplifier means 24 are provided for the detector signal $S_G$ comprising changes in the intensity of the initial light signal $S_0$. This embodiment also provides reasonable results, because the difference between the second measuring signal $S_{MA}$ of the embodiment of FIG. 7 (which is multiplied with a derivated detection signal) differs from the second measuring signal $S_{MA}$ of the embodiment of FIG. 6 (which is multiplied with a not derivated detection signal) only in the fact, that the derivated second measuring signal $S_{MA}$ is especially larger than the non-derivated second measuring signal $S_{MA}$ at small gas concentrations. The different phase results from that a derivation takes place or not.

According to the embodiment of FIG. 8 it is also possible to generate a third measuring signal $S_{MI1}$ additional to the first and second measuring signals $S_{MI}$ and $S_{MA}$ by using three lock-in amplifiers 19, 20, 21 and additional generating means 18 within the AC processing means 14. The generating means 18 generate a third modulation reference signal $S_f$ at the initial frequency f and then integrated over time, which is exactly defined in phase with the intensity variations of said initial light signal $S_0$. The third measuring signal $S_{MI1}$ is generated by multiplying the derivated detection signal $S_{D1}$, which is derivated by the derivator 25, with the third modulation reference signal $S_f$. The third measuring signal $S_{MI1}$ is a function of intensity of the initial light signal $S_0$ as described in the prior art, thus dependent on the temperature of the laser source. The two measuring signals $S_{MI}$ and $S_{MI1}$ provide more information, because the first measuring signal $S_{MI}$ represents the absolute intensity, whereas the third measuring signal $S_{MI1}$ represents the slope of the intensity of the initial light signal. In order to generate a final measuring signal with the processing unit 22 as described before, the first and third measuring signals $S_{MI}$ and $S_{MI1}$ are correlated by correlation means 26, connected with the processing means 22 to use the additional information provided by the two measuring signals $S_{MI}$ and $S_{MI1}$ for the resulting signal.

The invention claimed is:

1. Gas detection method comprising the following steps of
   providing an initial light signal ($S_0$), by a wavelength modulated laser source (1);
   providing an AC modulation signal at an initial frequency for wavelength modulation of said initial light signal ($S_0$) at said initial frequency (f) symmetrically around an absorption line of a gas the concentration or presence of which is to be determined;
   passing said initial light signal ($S_0$) having intensity variations over the time resulting from an alternative scanning around said gas absorption line through a gas detection region (4) intended for receiving at least one of said gases;
   receiving a resulting light signal ($S_G$) exciting said gas detection region (4) by detection means (8), said resulting light signal ($S_G$) comprises changes in the intensity of the initial light signal ($S_0$) due to the gas concentration in the detection region (4);
   generating a first modulation reference signal ($S_{2f0}$) at twice of said initial frequency and then integrated over time, whereby said first modulation reference signal ($S_{2f0}$) has a 45° phase angle to said initial light signal ($S_0$), and oscillates at an amplitude level being different from the amplitude level of said second modulation reference signal ($S_{2f1}$) between amplitude levels 1 and 0;
   generating a second modulation reference signal ($S_{2f}$, $S_{2f1}$) at twice of said initial frequency (f) and then integrated over time, whereby the second modulation reference signal ($S_{2f}$, $S_{2f1}$) has a defined amplitude level and a defined phase relationship with the intensity variations of said initial light signal ($S_0$);
   generating a first measuring signal ($S_{MI}$), which is a function of intensity of said initial light signal ($S_0$), said first measuring signal ($S_{MI}$) is generated by multiplying a detection signal ($S_{D0}$) directly received from said resulting light signal ($S_G$) with said first modulation reference signal ($S_{2f0}$);
   generating a second measuring signal ($S_{MA}$), which is a function of the gas absorption and substantially independent of an intensity modulation of said initial light signal at said initial frequency (f), said second measuring signal ($S_{MA}$) is generated by multiplying a second detection signal ($S_{D0}$, $S_{D1}$) received from said resulting light signal ($S_G$) with said second modulation reference signal ($S_{2f}$, $S_{2f1}$);
   providing a final measuring signal being independent from the intensity of light incident onto the detection means (8) by dividing said second measuring signal ($S_{MA}$) by said first measuring signal ($S_{MI}$) and thereby providing a signal relative to the presence or the concentration of a given gas.

2. A method according to claim 1, further defined by
   generating said second modulation reference signal ($S_{2f1}$) at twice of said initial frequency (f), and oscillating said second modulation reference signal ($S_{2f1}$) between amplitude levels 1 and −1, whereby said first and second modulation reference signals ($S_{2f0}$, $S_{2f1}$) have the same phase correlation to said initial light signal ($S_0$); and
   multiplying said second detection signal ($S_{D0}$) directly received from said resulting light signal ($S_G$) with said second modulation reference signal ($S_{2f1}$).

3. A method according to claim 1, further defined
   generating said second modulation reference signal ($S_{2f}$) at twice of said initial frequency (f), whereby said second modulation reference signal ($S_{2f}$) is exactly in phase with the intensity variations of said initial light signal ($S_0$);
   generating a second detection signal ($S_{D1}$) being substantially proportional to the time derivate of said resulting light signal ($S_G$); and
   generating said second measuring signal ($S_{MA}$) by multiplying said detection signal ($S_{D1}$) with said second modulation reference signal ($S_{2f}$).

4. A method according to claim 1, further defined
   generating a second detection signal ($S_{D1}$) being substantially proportional to the time derivate of said resulting light signal ($S_G$);
   generating a third modulation reference signal ($S_f$) at the initial frequency (f) and then integrated over time; whereby the third modulation reference signal ($S_f$) is exactly defined in phase with the intensity variations of said initial light signal ($S_0$);
   generating a third measuring signal ($S_{MI1}$) from said detection signal ($S_{D1}$), which is a function of intensity of said initial light signal ($S_0$), said third measuring signal ($S_{MI1}$) is generated by multiplying said detection signal ($S_{D1}$) with said third modulation reference signal ($S_f$);
   generating said second modulation reference signal ($S_{2f}$) at twice of said initial frequency (f) and then integrated over time, whereby the second modulation reference signal ($S_{2f}$) is exactly defined in phase with the intensity variations of said initial light signal ($S_0$);
   generating a second measuring signal ($S_{MA}$) from said detection signal ($S_{D1}$), which is a function of the gas absorption and substantially independent of an intensity modulation of said initial light signal at said initial frequency (F), said second measuring signal ($S_{MA}$) is generated by multiplying said second detection signal ($S_{D1}$) with said second modulation reference signal ($S_{2f}$).

5. A gas detector device comprising
   a least one wavelength modulated laser source (1) providing an initial light signal ($S_0$);
   a detection region (4) intended for receiving at least one gas the concentration or presence of which is to be determined;
   supply control means (13, 15) for wavelength modulating said initial light signal ($S_0$) at a initial frequency (f) symmetrically around an absorption line of one of said gases and providing said initial light signal ($S_0$) having intensity variation over the time, said supply control means comprise DC supply control means (13) for defining a DC current signal and AC supply control means (15) for defining an AC current signal at said given initial frequency (f) for generating an alternative scanning of light intensity of said initial light signal ($S_0$) around said gas absorption line;
   a light sensor (8) respectively arranged at the periphery of said detection region (4), said sensor (8) is intended for receiving a resulting light signal ($S_G$) comprising changes in the intensity of the initial light signal ($S_0$) having passed through said detection region (4) and providing a detection signal ($S_{D0}$, $S_{D1}$) proportional to the light intensity variation of said resulting light signal ($S_G$);
   processing means (19–26) for providing from said detection signal ($S_{D0}$, $S_{D1}$) a signal relative to the presence or the concentration of a given gas in said detection region (4), said processing means comprise first generating means (17, 18) for generating a first modulation reference signal ($S_{2f0}$, $S_f$) at a defined first frequency and second generating means (16) for generating a second modulation reference signal ($S_{2f1}$, $S_{2f1}$) at twice of said initial frequency (F);

first means (20, 21) for multiplying said first modulation reference signal ($S_{2f0}$, $S_f$) with said detection signal ($S_{D0}$, $S_{D1}$) and then integrating over time the resulting signal in order to provide a first measuring signal ($S_{MI}$, $S_{MC}$) which is a function of the intensity of said initial light signal ($S_0$) and substantially independent of the concentration of said gas;

second means (19) for multiplying said second modulation reference signal ($S_{2f1}$, $S_{2f}$) with said detection signal ($S_{D0}$, $S_{D1}$) and then integrating over time in order to provide a second measuring signal ($S_{MA}$) which is a function of the gas absorption and substantially independent of an intensity modulation of said initial light signal ($S_0$) at said initial frequency (f);

a processing unit (22) for dividing said second measuring signal ($S_{MA}$) by the first measuring signal ($S_{MI}$, $S_{MIC}$) for providing the signal relative to the presence of a given gas or to its concentration; whereby said light sensor (8) is connected to said first means (20) for multiplying said first modulation reference signal ($S_{2f0}$) and thus providing said resulting light signal ($S_G$) as detection signal ($S_{D0}$);

said first generating means (17) generate a first modulation reference signal ($S_{2f0}$) at twice of said initial frequency (f) with a 45° phase angle to said initial light signal ($S_0$) and oscillate said first modulation reference signal ($S_{2f0}$) between amplitude levels 1 and 0.

6. The gas detector device according claim 5, whereby said second generating means (16) generate said second modulation reference signal ($S_{2f1}$) at twice of said initial frequency (f) with a 45° phase angle to said initial light signal ($S_0$) and oscillate said second modulation reference signal ($S_{2f1}$) between amplitude levels 1 and −1.

7. The gas detector device according claim 5 whereby said processing means comprise means (25) for providing a detection signal ($S_{D1}$) substantially proportional to the time derivate of said resulting light signal ($S_G$);

said second generating means (16) generate a second modulation reference signal ($S_{2f}$) at twice of said initial frequency (f) exactly in phase with the intensity variations of said initial light signal ($S_0$); and wherein said first means (20) for multiplying said first modulation reference signal ($S_{2f0}$) with said detection signal ($S_{D0}$, $S_{D1}$) receive said resulting light signal ($S_G$) as detection signal ($S_{D0}$), and wherein said second means (19) for multiplying said second modulation reference signal ($S_{2f}$) with said detection signal ($S_{D0}$, $S_{D1}$) receive the detection signal ($S_{D1}$) substantially proportional to the time derivate of said resulting light signal ($S_G$).

8. The gas detector device according claim 7 whereby third means (18) for generating a third modulation reference signal ($S_f$) at said initial frequency (f) exactly in phase with the intensity variations of said initial light signal ($S_0$), third means (21) for multiplying said third modulation reference signal ($S_f$) with said detection signal ($S_{D1}$), substantially proportional to the time derivate of said resulting light signal ($S_G$), and then integrating over time the resulting signal in order to provide a third measuring signal ($S_{MI1}$) which is a function of the intensity of said initial light signal ($S_0$) and substantially independent of the concentration of said gas, a processing unit (22, 26) for correlating said first measuring signal ($S_{MI}$) with said third measuring signal ($S_{MI1}$) and for dividing said second measuring signal ($S_{MA}$) by the correlated measuring signal ($S_{MIC}$) for providing the signal relative to the presence of a given gas or to its concentration.

* * * * *